US012655170B2

(12) United States Patent
Xia et al.

(10) Patent No.: US 12,655,170 B2
(45) Date of Patent: Jun. 16, 2026

(54) DEVICE AND METHOD FOR PRODUCING SUCROSE-6-ESTER

(71) Applicant: ANHUI JINHE INDUSTRIAL CO., LTD., Chuzhou (CN)

(72) Inventors: Jiaxin Xia, Chuzhou (CN); Zhengsong Zhang, Chuzhou (CN); Jingang Zhao, Chuzhou (CN); Zhenghua Li, Chuzhou (CN); Congyong Zhang, Chuzhou (CN); Xuelian Zheng, Chuzhou (CN); Yongfeng Bu, Chuzhou (CN)

(73) Assignee: ANHUI JINHE INDUSTRIAL CO., LTD., Chuzhou (CN)

( * ) Notice: Subject to any disclaimer, the term of this patent is extended or adjusted under 35 U.S.C. 154(b) by 655 days.

(21) Appl. No.: 18/003,505

(22) PCT Filed: Jan. 25, 2021

(86) PCT No.: PCT/CN2021/073552
§ 371 (c)(1),
(2) Date: Dec. 28, 2022

(87) PCT Pub. No.: WO2022/155947
PCT Pub. Date: Jul. 28, 2022

(65) Prior Publication Data
US 2023/0234980 A1 Jul. 27, 2023

(51) Int. Cl.
*C07H 13/04* (2006.01)
*B01J 19/18* (2006.01)

(52) U.S. Cl.
CPC .......... *C07H 13/04* (2013.01); *B01J 19/1887* (2013.01); *B01J 2219/00153* (2013.01)

(58) Field of Classification Search
CPC . C07H 13/04; C07H 1/00; C07H 13/06; B01J 19/1887; B01J 2219/00153; B01J 2219/00051; B01J 2219/00135; B01J 2219/00155; Y02P 20/10
USPC ....................................................... 422/198
See application file for complete search history.

(56) References Cited

U.S. PATENT DOCUMENTS 9,073,959 B2 * 7/2015 Micinski et al. ...... C07H 13/04

* cited by examiner

*Primary Examiner* — Prem C Singh
(74) *Attorney, Agent, or Firm* — Chiesa Shahinian & Giantomasi PC

(57) ABSTRACT

Provided are a device and a method for producing a sucrose-6-ester. The device includes a shell, a film scraping apparatus, and a base, wherein the film scraping apparatus is arranged on the base, and the shell covers the film scraping apparatus and the base; the shell is provided with a reaction solution inlet and a condensated water outlet; the base is provided with a carboxylate feed pipe, a reaction product discharge pipe, and a reaction channel connected to the carboxylate feed pipe; the film scraping apparatus includes a temperature control unit, a rotary tube, and a plurality of scrapers arranged on an inner wall of the rotary tube, and an outer edge of each of the scrapers abuts against an outer wall of the temperature control unit; and the rotary tube is able to rotate around the temperature control unit.

8 Claims, 6 Drawing Sheets

100

Figure 9:
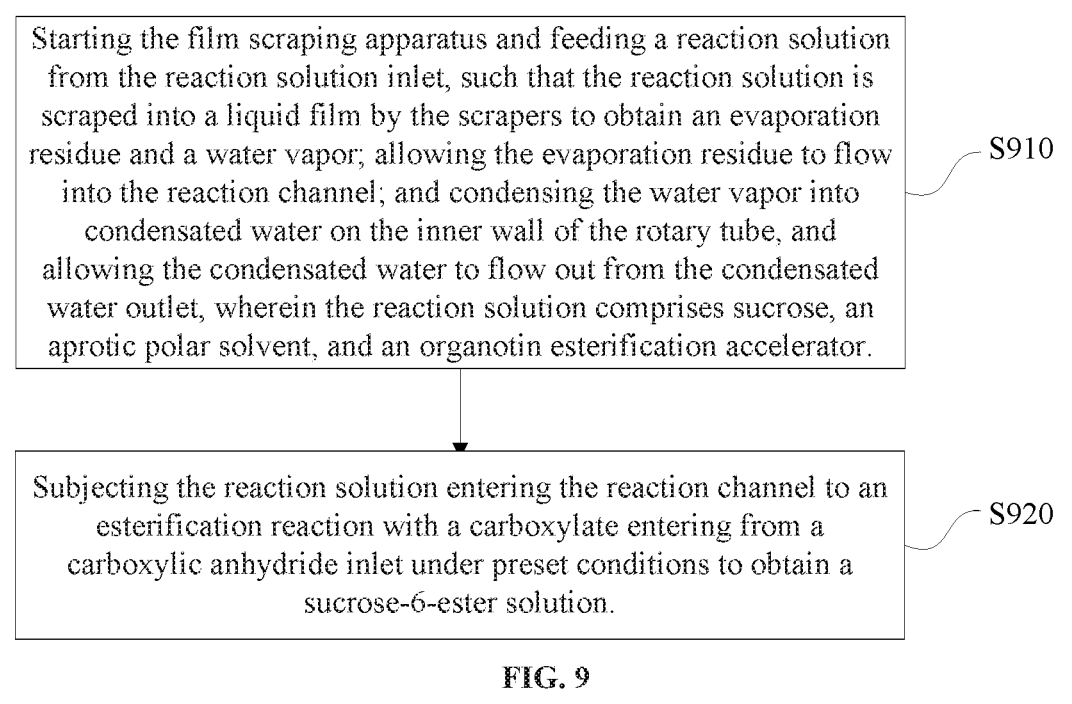

Starting the film scraping apparatus and feeding a reaction solution from the reaction solution inlet, such that the reaction solution is scraped into a liquid film by the scrapers to obtain an evaporation residue and a water vapor; allowing the evaporation residue to flow into the reaction channel; and condensing the water vapor into condensated water on the inner wall of the rotary tube, and allowing the condensated water to flow out from the condensated water outlet, wherein the reaction solution comprises sucrose, an aprotic polar solvent, and an organotin esterification accelerator.

S910

Subjecting the reaction solution entering the reaction channel to an esterification reaction with a carboxylate entering from a carboxylic anhydride inlet under preset conditions to obtain a sucrose-6-ester solution.

DEVICE AND METHOD FOR PRODUCING SUCROSE-6-ESTER

CROSS-REFERENCE TO RELATED APPLICATIONS

This application is a National Stage under 35 U.S.C. 371 of International Patent Application No. PCT/CN2021/073552, filed Jan. 25, 2021; the disclosure of which is incorporated herein by reference in its entirety.

TECHNICAL FIELD

The present disclosure belongs to the technical field of fine chemical industry, and in particular relates to a device and a method for producing a sucrose-6-ester.

BACKGROUND ART

Sucralose is a new sweetener with advantages such as high sweetness, no calories, high stability, and high safety, and has very promising market prospects. Sucralose-6-ester is an important intermediate in the production of sucralose.

In the prior art, a process for synthesizing a sucrose-6-ester mainly includes: mixing sucrose, an aprotic polar solvent, and an organotin esterification accelerator to obtain a first reaction mixture; removing moisture from the first reaction mixture by contacting the first reaction mixture with a gas or solvent vapor capable of removing water for a specified period of time at a specific temperature and pressure to obtain a second reaction mixture; adding a carboxylic anhydride into the second reaction mixture to obtain a third reaction mixture; and subjecting the third reaction mixture to a reaction for sufficient time to obtain the sucrose-6-ester. This process requires the use of the gas or solvent vapor capable of removing water, which seriously affects the continuity of a sucrose-6-ester production process, prolongs the production cycle, and reduces the production efficiency. In addition, the consumption of a large amount of the gas or solvent capable of removing water greatly increases the production cost and energy consumption.

It should be noted that the statements herein merely provide background information related to the present disclosure and do not necessarily constitute the prior art.

SUMMARY

In view of the above problems, the present disclosure provides a device and a method for producing a sucrose-6-ester, which make it possible to overcome the above problems or at least partially solve the problems.

According to an aspect of the present disclosure, the present disclosure provides a device for producing a sucrose-6-ester, including: a shell, a film scraping apparatus, and a base, wherein the film scraping apparatus is arranged on the base, and the shell covers the film scraping apparatus and the base;

the shell is provided with a reaction solution inlet and a condensated water outlet; the base is provided with a carboxylate feed pipe, a reaction product discharge pipe, and a reaction channel connected to the carboxylate feed pipe;

the film scraping apparatus includes a temperature control unit, a rotary tube, and a plurality of scrapers arranged on an inner wall of the rotary tube, and an outer edge of each of the scrapers abuts against an outer wall of the temperature control unit; and the rotary tube is able to rotate around the temperature control unit, such that a reaction solution entering from the reaction solution inlet and flowing downward along the outer wall of the temperature control unit is scraped into a liquid film on the outer wall of the temperature control unit by using the scrapers to obtain an evaporation residue and a water vapor.

In some embodiments, in the device, the temperature control unit is a cylindroid that is arranged coaxially with the rotary tube and composed of a fan-closed heating chamber and a fan-closed cooling chamber, and the fan-closed heating chamber and the fan-closed cooling chamber are separated by a thermal insulation plate.

In some embodiments, in the device, a diameter of the fan-closed cooling chamber is greater than a diameter of the fan-closed heating chamber; and the plurality of scrapers are elastic metal sheets, and outer edge ends of the plurality of scrapers are arc-shaped.

In some embodiments, in the device, the rotary tube is fixedly provided with an inner gear ring on an upper end of the rotary tube; and the shell is provided with a motor penetrating through the shell, the motor is provided with a gear wheel at an end of a rotating shaft of the motor, and the gear wheel meshes with the inner gear ring.

In some embodiments, in the device, a cooling unit is fixedly provided at a position on an inner wall of the shell corresponding to the fan-closed heating chamber.

In some embodiments, in the device, the plurality of scrapers are L-shaped scrapers; one end of each of the L-shaped scrapers is an arrangement end arranged at an upper end of an inner wall of the rotary tube, and the other end of each of the L-shaped scrapers is an extension end arranged in contact with an upper surface of the base; and a drainage port is formed at a position on a lower end of the inner wall of the rotary tube corresponding to each of the L-shaped scraper, a drainage plate is provided corresponding to the drainage port, and the drainage plate, the corresponding drainage port, and a corresponding part of the rotary tube form a condensated water channel.

In some embodiments, in the device, the base includes an upper base and a lower base that are arranged in close contact; a gradually-inclined circular reaction channel is provided from an upper surface to a lower surface of a bottom of the upper base; a first feed port and a second feed port are formed at an upwardly-inclined end of the reaction channel; the first feed port is configured to receive the evaporation residue and the second feed port is connected to the carboxylate feed pipe; and a discharge port is formed at a downwardly-inclined end of the reaction channel, and the discharge port is connected to the reaction product discharge pipe penetrating through the lower base.

In some embodiments, in the device, a rotation direction of the rotary tube is opposite to an inclination direction of the reaction channel.

In some embodiments, in the device, the shell is further provided with a vacuum tube, and the vacuum tube is able to be connected to a vacuum pump.

According to another aspect of the present disclosure, the present disclosure provides a method for producing a sucrose-6-ester, which is implemented by using the device described above, and includes:

separation of a reaction solution: starting the film scraping apparatus and feeding a reaction solution from the reaction solution inlet, such that the reaction solution is scraped into a liquid film by the scrapers to obtain an evaporation residue and a water vapor; allowing the evaporation residue to flow into the reaction channel; and condensing the water vapor into condensated water on the inner wall of the rotary tube, and allowing the condensated water to flow out from the condensated water outlet, where the reaction solution includes sucrose, an aprotic polar solvent, and an organotin esterification accelerator; and esterification reaction: subjecting the reaction solution entering the reaction channel to an esterification reaction with a carboxylate entering from a carboxylic anhydride inlet under preset conditions to obtain a sucrose-6-ester-containing solution.

In summary, the present disclosure has the following beneficial effects:

A production device provided with a film scraping apparatus is designed. Scrapers of the film scraping apparatus can rotate around a temperature control unit, such that a reaction solution on an outer wall of the temperature control unit is scraped into a liquid film to obtain a water vapor and an evaporation residue, thus achieving the purpose of removing the moisture in a prepared sucrose-6-ester reaction solution. In addition, during a continuous rotation process of the film scraping apparatus, the evaporation residue free of moisture continuously enters the reaction channel to undergo an esterification reaction, and a reaction raw material can be continuously fed into the production device to realize the continuous production of a sucrose-6-ester, which greatly shortens the production cycle and improves the production efficiency of the sucrose-6-ester. Moreover, the device of the present disclosure allows for realizing of design integration of a separation unit and a reaction unit, which reduces a volume and a floor space of the production device. With the integrated design, there is no need to press a separated reaction solution into another reactor, which reduces the energy consumption and overcomes the defect in the prior art that a second reaction mixture needs to be injected into another space and then mixed with a carboxylic anhydride. Since the moisture in the reaction solution can be effectively removed without a gas or solvent vapor capable of removing water, the production cost can be greatly reduced while ensuring a sucrose-6-ester yield.

The above description is merely a summary of the technical solutions of the present disclosure. In order to allow the technical means of the present disclosure to be understood clearly and implemented in accordance with the content of the specification and allow the above and other objectives, features, and advantages of the present disclosure to be obvious and easy to be understood, specific implementations of the present disclosure are described below.

BRIEF DESCRIPTION OF THE DRAWINGS

By reading the detailed description of the following preferred embodiments, various other advantages and benefits will become apparent to those of ordinary skill in the art. The accompanying drawings are provided merely to illustrate the preferred embodiments, rather than to limit the present disclosure. Throughout the accompanying drawings, the same reference numeral represents the same component. In the accompanying drawings:

FIG. 9 is a schematic flow chart of a method for producing a sucrose-6-ester according to an embodiment of the present disclosure.

DETAILED DESCRIPTION OF THE EMBODIMENTS

Exemplary embodiments of the present disclosure will be described in detail below with reference to the accompanying drawings. Although the accompanying drawings show exemplary embodiments of the present disclosure, it should be understood that the present disclosure may be implemented in various forms and should not be limited to the embodiments set forth herein. Instead, these embodiments are provided to provide a thorough understanding of the present disclosure, and a scope of the present disclosure can be fully conveyed to those skilled in the art.

The concept of the present disclosure is as follows:

In the prior art, a reaction solution for producing a sucrose-6-ester needs to first undergo moisture removal with a vapor or solvent in a reactor, and then is pressed into another reactor to react with a carboxylic anhydride to obtain the sucrose-6-ester. In the above process, the moisture removal with the vapor or solvent requires a high energy consumption, bulky equipment, and a large floor space, and can only lead to insufficient moisture removal; after the moisture is removed, the reaction solution also needs to be pressed into another reactor to undergo an esterification reaction, which requires additional energy and time and reduces the production efficiency of the sucrose-6-ester; and the production process of the prior art is discontinuous, and the next reaction can only be conducted after the previous reaction is completed, which also seriously affects the production efficiency of the sucrose-6-ester.

Figure 1:
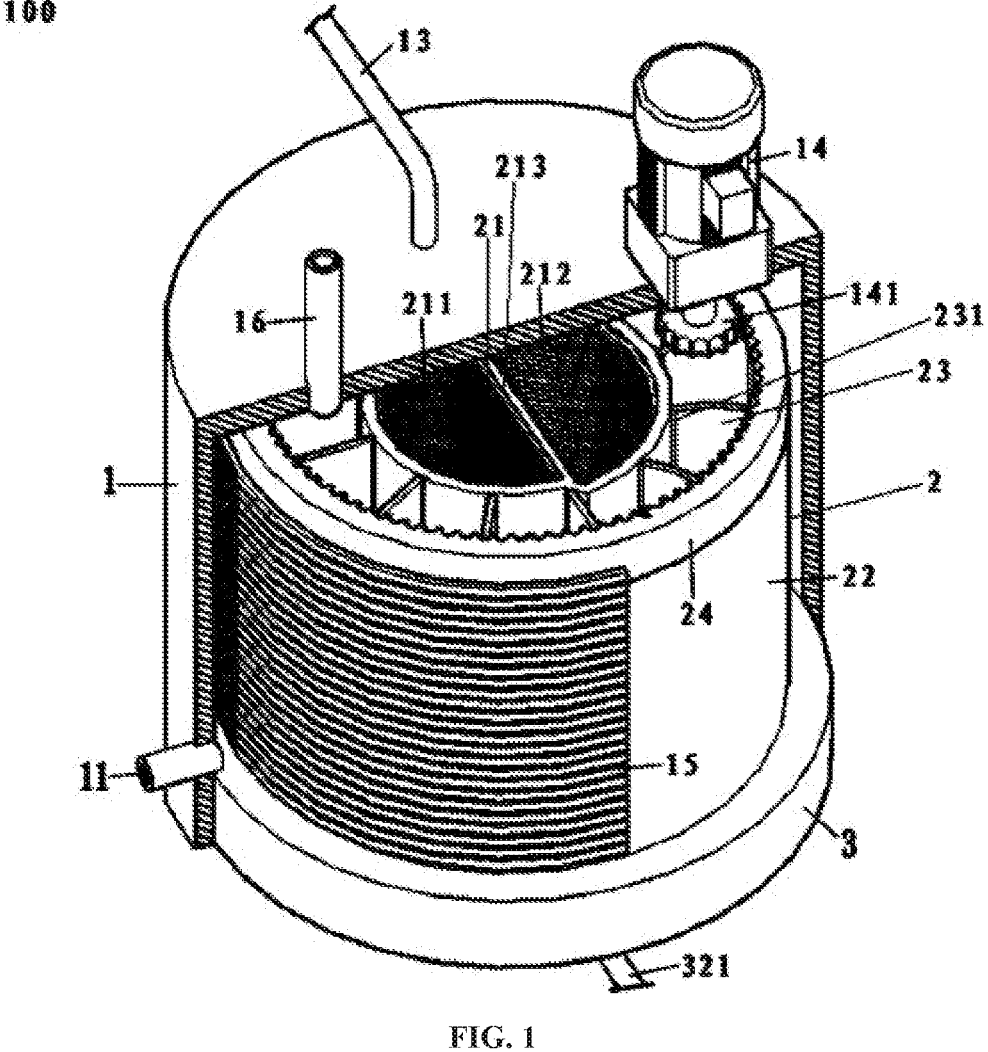
FIG. 1 is a schematic diagram illustrating a three-dimensional (3D) structure of a device for producing a sucrose-6-ester according to an embodiment of the present disclosure, in which a half of a shell of the device is cut off.
Figure 2:
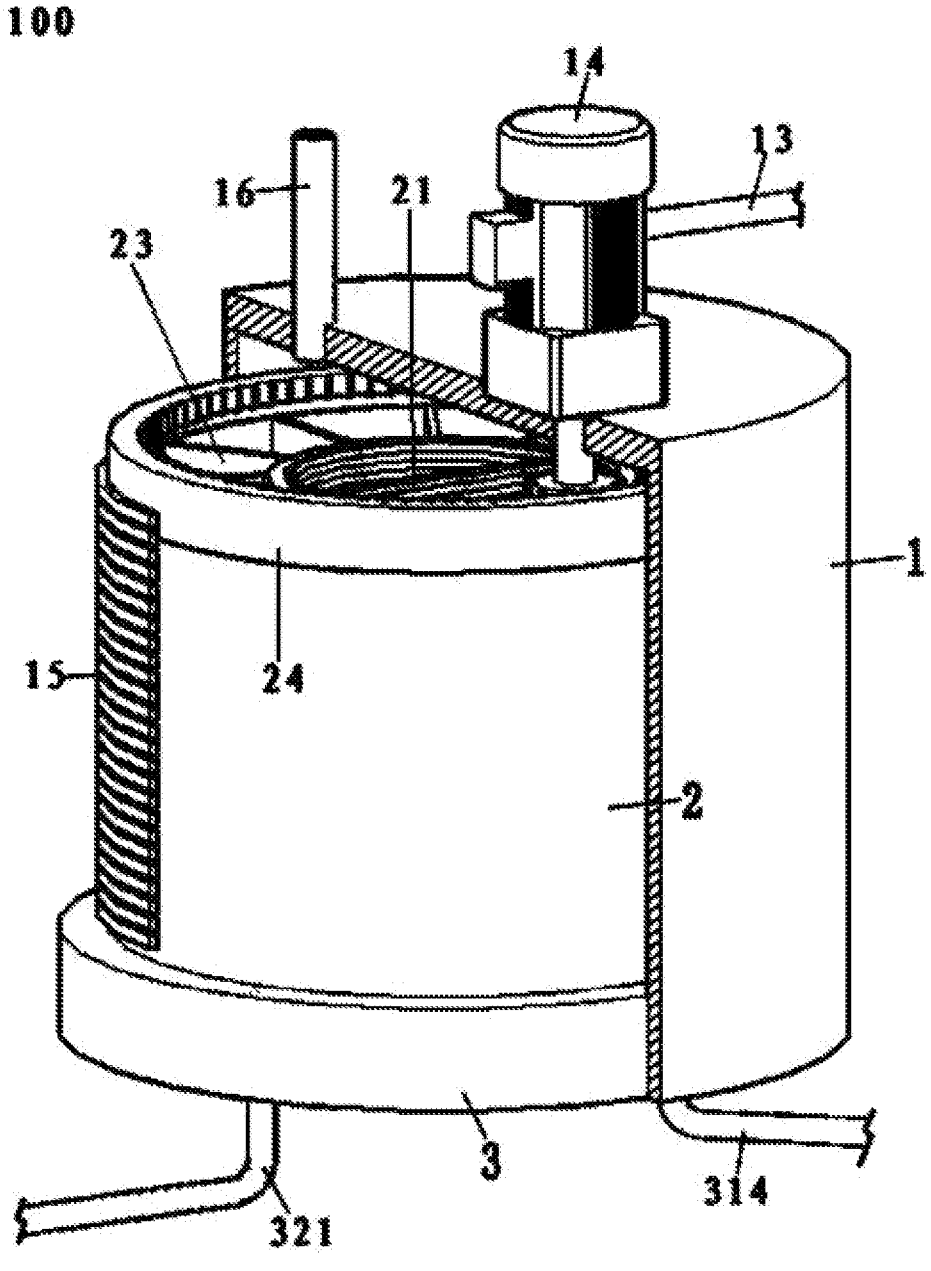
FIG. 2 is a schematic diagram illustrating a 3D structure of a device for producing a sucrose-6-ester according to another embodiment of the present disclosure, in which a half of a shell of the device is cut off.
Figures 3, 4:
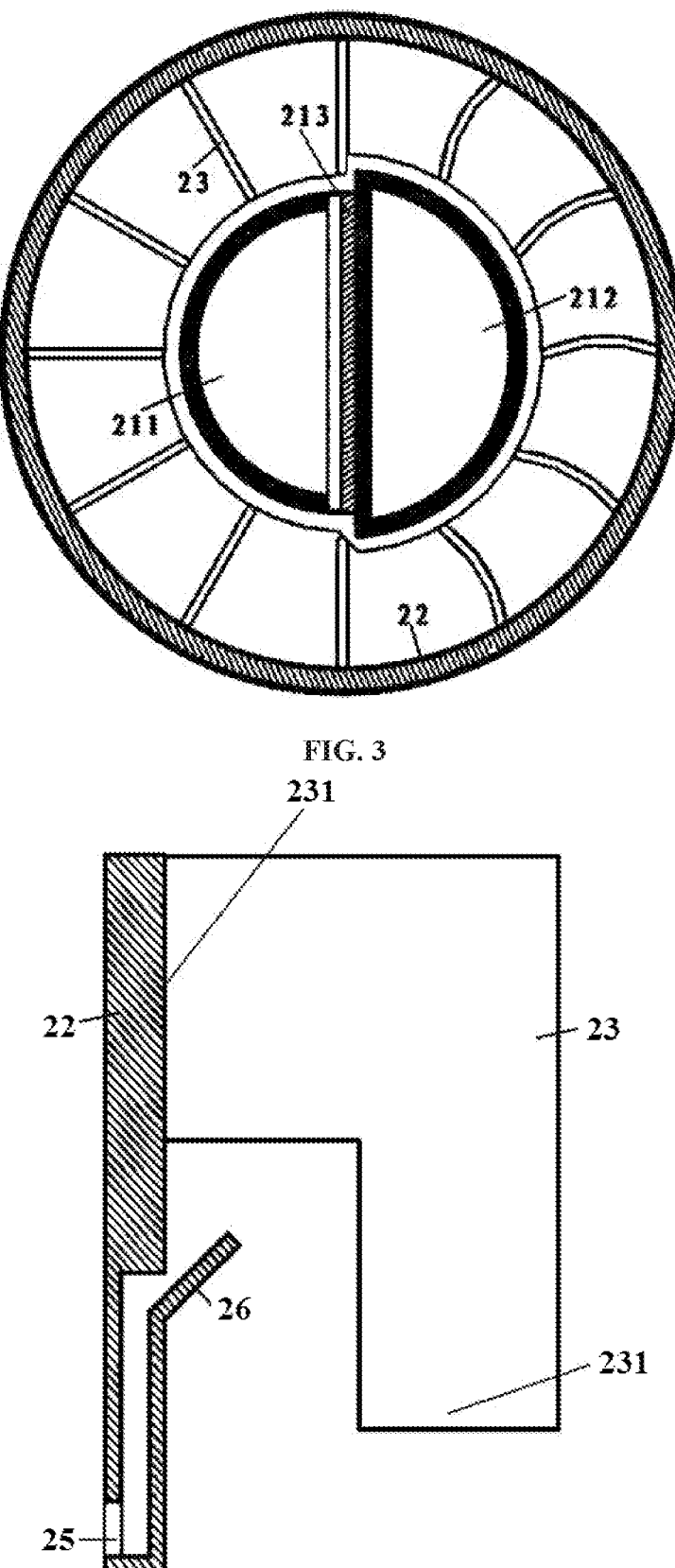
FIG. 3 is a schematic top view illustrating an internal structure of a rotary unit of a device for producing a sucrose-6-ester according to an embodiment of the present disclosure.
FIG. 4 is a schematic side view illustrating a structure of a scraper 23 of a device for producing a sucrose-6-ester according to an embodiment of the present disclosure.
Figures 5, 6:
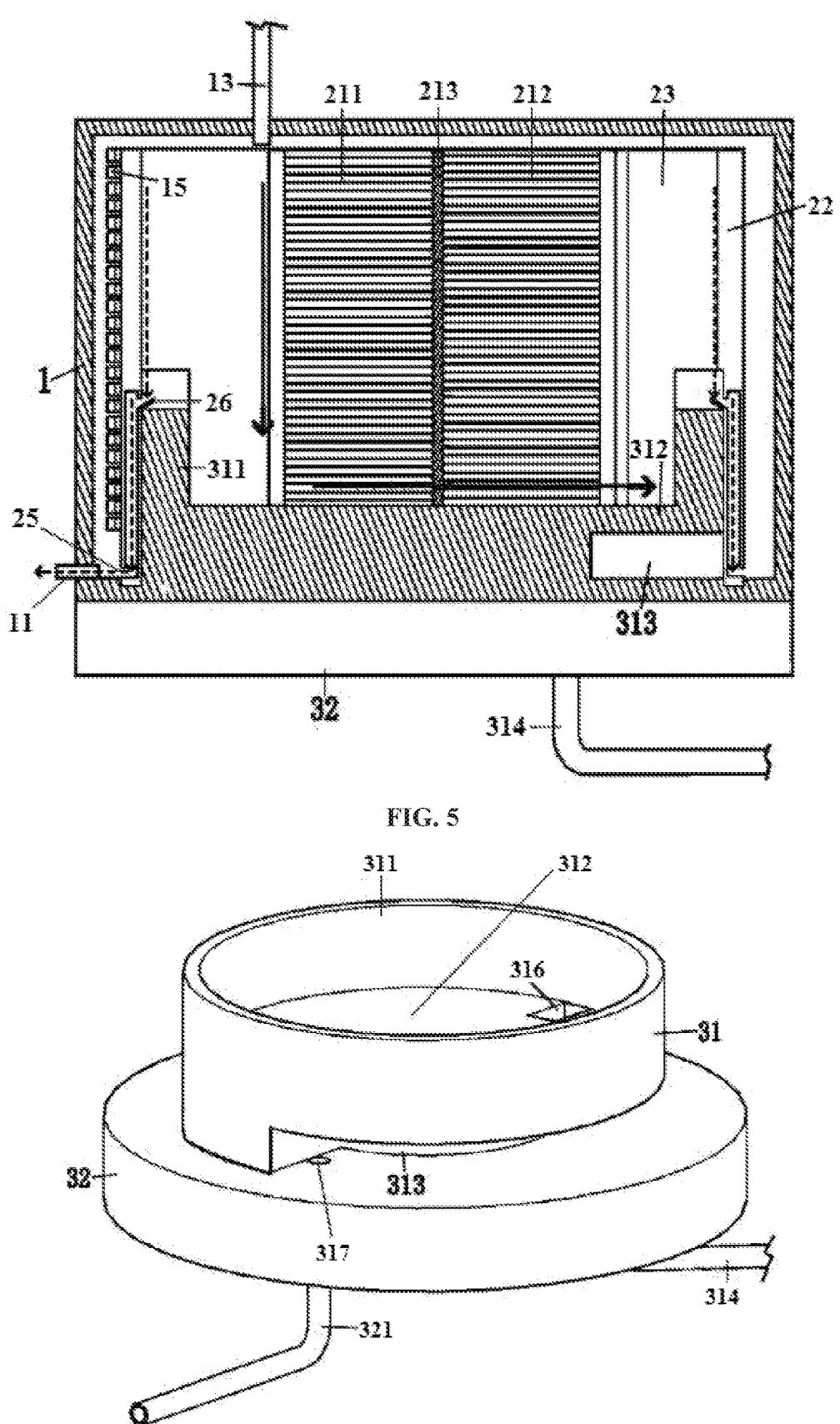
FIG. 5 is a schematic sectional view illustrating a structure of a device for producing a sucrose-6-ester according to an embodiment of the present disclosure.
FIG. 6 is a schematic diagram illustrating a 3D structure of a base 3 of a device for producing a sucrose-6-ester according to an embodiment of the present disclosure.
Figures 7, 8:
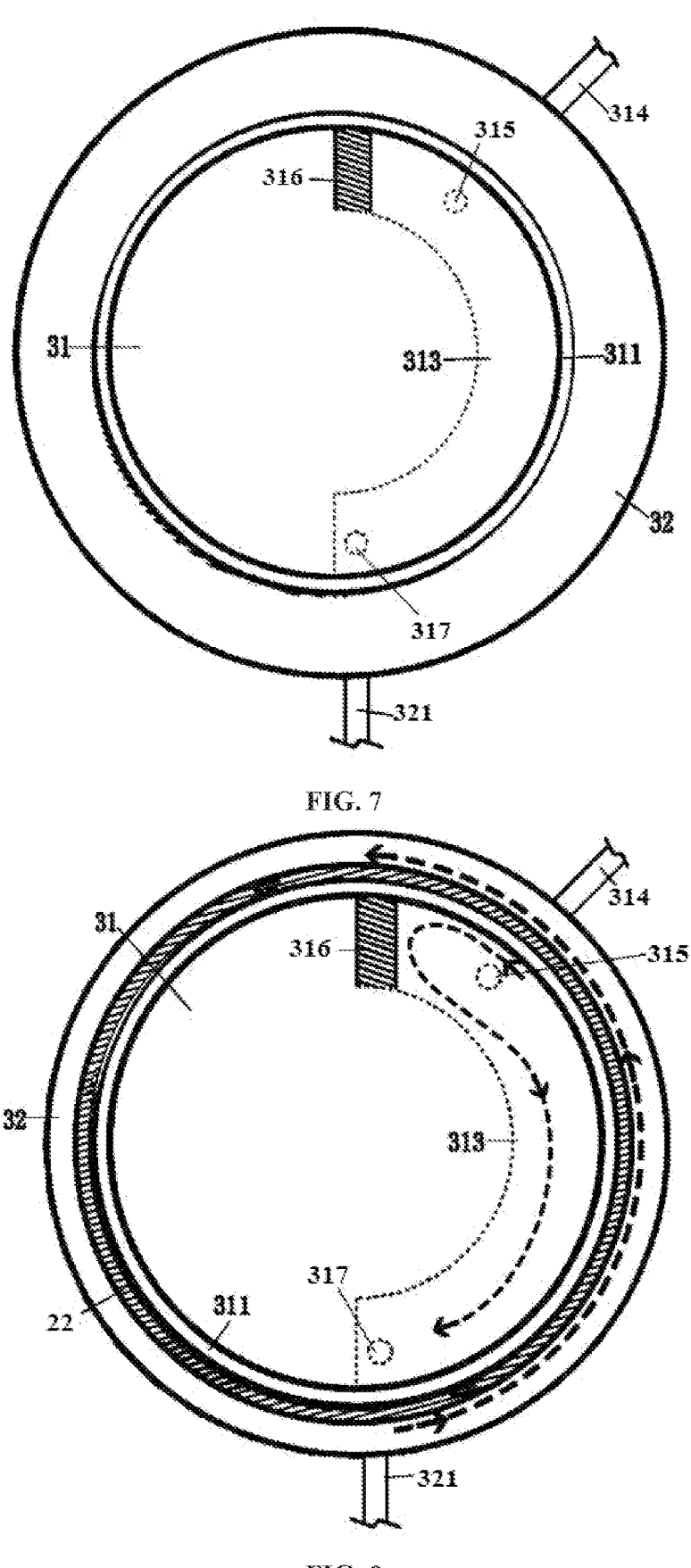
FIG. 7 is a schematic top view illustrating a structure of a base 3 of a device for producing a sucrose-6-ester according to an embodiment of the present disclosure.
FIG. 8 is a schematic diagram illustrating a material flow direction in a base 3 of a device for producing a sucrose-6-ester according to an embodiment of the present disclosure.

FIG. 1 is a schematic diagram illustrating a 3D structure of a device for producing a sucrose-6-ester according to an embodiment of the present disclosure, in which a half of a shell of the production device is cut off; FIG. 2 is a schematic diagram illustrating a 3D structure of a device for producing a sucrose-6-ester according to another embodiment of the present disclosure, in which a half of a shell of the device is cut off; FIG. 3 is a schematic top view illustrating an internal structure of a rotary unit of a device for producing a sucrose-6-ester according to an embodiment of the present disclosure; FIG. 4 is a schematic side view illustrating a structure of a scraper 23 of a device for producing a sucrose-6-ester according to an embodiment of the present disclosure; FIG. 5 is a schematic sectional view illustrating a structure of a device for producing a sucrose-6-ester according to an embodiment of the present disclosure; FIG. 6 is a schematic diagram illustrating a 3D structure of a base 3 of a device for producing a sucrose-6-ester according to an embodiment of the present disclosure; FIG. 7 is a schematic top view illustrating a structure of a base 3 of a device for producing a sucrose-6-ester according to an embodiment of the present disclosure; and FIG. 8 is a schematic diagram illustrating a material flow direction in a base 3 of a device for producing a sucrose-6-ester according to an embodiment of the present disclosure.

As shown in FIGS. 1 to 8, the device 100 for producing a sucrose-6-ester includes: a shell 1, a film scraping apparatus 2, and a base 3, wherein the film scraping apparatus 2 is arranged on the base 3 and the shell 1 covers the film scraping apparatus 2 and the base 3;

the shell 1 is provided with a reaction solution inlet 13 and a condensated water outlet 11; the base 3 is provided with a carboxylate feed pipe 314, a reaction product discharge pipe 321, and a reaction channel 313 connected to the carboxylate feed pipe 314;

the film scraping apparatus 2 includes a temperature control unit 21, a rotary tube 22, and a plurality of scrapers 23 arranged on an inner wall of the rotary tube 22, and an outer edge 231 of each of the scrapers 23 abuts against an outer wall of the temperature control unit 21; and the rotary tube 22 is able to rotate around the temperature control unit 21, such that a reaction solution entering from the reaction solution inlet 13 and flowing downward along the outer wall of the temperature control unit 21 is scraped into a liquid film on the outer wall of the temperature control unit 21 by using the scrapers 23 to obtain an evaporation residue and a water vapor.

It should be noted that, in order to ensure that the reaction solution will not remain on an upper surface of the base 3, when the film scraping apparatus 2 is arranged on the base 3, a lower end of the temperature control unit 21 may tightly fit exactly the upper surface of the base 3.

With the above device, a process for producing a sucrose-6-ester may be described as follows: the rotary tube 22 is started, and the rotary tube 22 drives the plurality of scrapers 23 on its inner wall to rotate around the outer wall of the temperature control unit 21; a reaction solution is fed from the reaction solution inlet 13, wherein the reaction solution is a mixed solution of raw materials for producing the sucrose-6-ester and may at least include sucrose, an aprotic polar solvent, and an organotin esterification accelerator; due to the combined action of gravity and a scraping force of the scrapers, the reaction solution forms a very thin liquid film on the outer wall of the temperature control unit 21, and during this process, moisture is evaporated into a water vapor, the water vapor is condensed into liquid water at the inner wall of the rotary tube 22, and the liquid water flows downward along the inner wall of the rotary tube 22 and then is discharged from the condensated water outlet 11; and a reaction solution after removing moisture is called an evaporation residue, and the evaporation residue is further scraped and gradually moves downward along the inner wall of the rotary tube 22 to the first feed port of the reaction channel 313, and then enters the reaction channel 313 to undergo an esterification reaction with a carboxylate entering from the carboxylate feed pipe 314 to obtain a mixed solution containing a sucrose-6-ester as the main product.

It can be seen from the device in FIG. 1 that a production device provided with a film scraping apparatus is designed in the present disclosure. Scrapers of the film scraping apparatus can rotate around a temperature control unit, such that a reaction solution on an outer wall of the temperature control unit is scraped into a liquid film to obtain a water vapor and an evaporation residue, thus achieving the purpose of removing moisture in a prepared sucrose-6-ester reaction solution. In addition, during a continuous rotation process of the film scraping apparatus, the evaporation residue free of moisture continuously enters the reaction channel to undergo an esterification reaction, and a reaction raw material can be continuously fed into the production device to realize the continuous production of a sucrose-6-ester, which greatly shortens the production cycle and improves the production efficiency of the sucrose-6-ester. Moreover, the device of the present disclosure realizes a design integrating a separation unit and a reaction unit, which reduces a volume and a floor space of the production device. With the integrated design, there is no need to press a separated reaction solution into another reactor, which reduces the energy consumption and overcomes the defect in the prior art that a second reaction mixture needs to be injected into another space and then mixed with a carboxylic anhydride. Since moisture in the reaction solution can be effectively removed without a gas or solvent vapor capable of removing water, the production cost can be greatly reduced while ensuring a sucrose-6-ester yield.

In the following embodiments of the present disclosure, the scrapers may be elastic metal sheets; a length of each of the scrapers is no less than a distance between the inner wall of the rotary tube 22 and the outer wall of the temperature control unit 21; the scrapers may be bent during a process of the scrapers to scrape the reaction solution; during the bending of the scrapers, there will be elastic energy storage in the scrapers; during the scraping process, the stored elastic energy can be converted into an action force for scraping the reaction solution, and the greater the stored elastic energy, the greater the action force; a strength of the action force directly determines a thickness of the liquid film, and the thicker the liquid film, the slower the water evaporation, the more incomplete the water removal, and the thinner the liquid film, the faster the water evaporation, the more thorough the water removal. Therefore, it is preferred to prepare the scrapers from a material with relatively-high elasticity, which can be specifically manganese steel or the like. The elastic energy storage in the scrapers not only is related to a material for the scrapers, but also depends on a size and thickness of the scrapers, and the size and thickness of the scrapers can be determined according to a size of the overall device. In some embodiments of the present disclosure, a length of each of the scrapers may be, but is not limited to, $1/3$ to $2/3$ of a radius of the rotary tube; and a thickness of each of the scrapers may be, but is not limited to, $1/500$ to $1/100$ of the length of the scraper. It should be noted that the length and thickness of the scrapers are related to many factors, and the above parameters are only provided as preferred solutions for reference; and the length and thickness of the scrapers can be determined according to many factors such as device size, device power, and expected production scale, and are not limited by the present disclosure.

In order to extend the service life of the scraper and temperature control unit, in some embodiments of the present disclosure, an outer edge end of the scraper may be designed to be arc-shaped to reduce friction; and a plurality of scrapers can be evenly arranged on the inner wall of the rotary tube, and a number of the scrapers may be, but is not limited to, 4 to 20.

FIG. 3 is a schematic top view illustrating an internal structure of a rotary unit of a device for producing a sucrose-6-ester according to an embodiment of the present disclosure. It can be seen from FIG. 3 that, in some embodiments of the present disclosure, the temperature control unit 21 is a cylindroid that is arranged coaxially with the rotary tube 22 and composed of a fan-closed heating chamber 211 and a fan-closed cooling chamber 212, and the fan-closed heating chamber 211 and the fan-closed cooling chamber 212 are separated by a thermal insulation plate 213.

Since evaporating moisture from the reaction solution may be occur at a temperature different from that of the esterification reaction, in order to thoroughly remove the moisture as soon as possible, the reaction solution usually needs to be heated to 50° C. or higher, but the esterification reaction usually needs to be conducted at a lower temperature. For example, in some embodiments, the esterification reaction may be conducted at a temperature of 0° C. to 50° C.; and in some other embodiments, the esterification reaction may be conducted at a temperature of 5° C. to 20° C. In order to make the reaction solution have a temperature suitable for the esterification reaction when entering the reaction channel, in this embodiment, the cylindroid temperature control unit 21 is divided into a fan-closed heating chamber 211 and a fan-closed cooling chamber 212 that are separated by a thermal insulation plate 213.

Since an outer wall of the fan-closed heating chamber 211 needs to be heated, in order to prevent the fan-closed heating chamber 211 from penetrating through the thermal insulation plate 213 and further reduce the energy consumption, a position of the fan-closed heating chamber 211 corresponding to the thermal insulation plate 213 may not be filled with a heating medium. The heating medium of the fan-closed heating chamber 211 may be water, oil, or a resistance wire. With water as an example, conduits with water may be vertically arranged along a radial direction of the fan-closed heating chamber 211 at the inner wall of the fan-closed heating chamber 211, wherein water enters from an opening at a lower end of each conduit and exits from an opening at an upper end of each conduit. Any existing technique that can achieve the above purpose may be adopted, and is not detailed here.

A cooling medium in the fan-closed cooling chamber 212 may be water or air, which may be filled in inner conduits of the fan-closed cooling chamber 212; and the conduits may be arranged vertically or horizontally, which will not be repeated.

As shown in FIG. 3, in some embodiments of the present disclosure, a diameter of the fan-closed cooling chamber 212 is greater than a diameter of the fan-closed heating chamber 211.

With the temperature control unit 21 divided into a fan-closed heating chamber 211 and a fan-closed cooling chamber 212, when the reaction solution flows along outer walls of the fan-closed heating chamber 211 and the fan-closed cooling chamber 212, different purposes need to be achieved. When flowing along an outer wall of the fan-closed heating chamber 211, the reaction solution is scraped by using the scrapers into a liquid film to achieve the separation of water and an evaporation residue. When flowing along an outer wall of the fan-closed cooling chamber 212, the evaporation residue is cooled to a temperature suitable for the esterification reaction, and ideally, the evaporation residue is totally scraped to the inlet of the reaction channel 313, specifically to the first feed port 316 (as shown in FIG. 6). In order to achieve the above purpose, a diameter of the fan-closed cooling chamber 212 is set to be greater than a diameter of the fan-closed heating chamber 211, the scrapers 23 have a length that is no less than a distance between the inner wall of the rotary tube 22 and the outer wall of the fan-closed heating chamber 211, such that a bending degree of the scrapers 23 when at positions corresponding to the outer wall of the fan-closed heating chamber 211 is smaller than a bending degree of the scrapers 23 when at positions corresponding to the outer wall of the fan-closed cooling chamber 212; the elastic energy storage of the scrapers 23 when at positions corresponding to the outer wall of the fan-closed cooling chamber 212 is greater than the elastic energy storage of the scrapers 23 when at positions corresponding to the outer wall of the fan-closed heating chamber 211; and an action force for the scrapers 23 to scrape the reaction solution when the scrapers are at positions corresponding to the outer wall of the fan-closed cooling chamber 212 is greater than an action force for the scrapers to scrape the reaction solution when the scrapers are at positions corresponding to the outer wall of the fan-closed heating chamber 211. The reaction solution is scraped into a liquid film at the outer wall of the fan-closed heating chamber 211, and can be almost completely scraped at the outer wall of the fan-closed cooling chamber 212 to move along a rotation direction of the film scraping apparatus, and the reaction solution tumbles among the plurality of scrapers 23 until moving to the inlet of the reaction channel.

As shown in FIG. 1 and FIG. 2, the rotary tube 22 is fixedly provided with an inner gear ring 24 at an upper end of the rotary tube 22; and the shell 1 is provided with a motor 14 penetrating through the shell, the motor 14 is provided with a gear wheel 141 at an end of a rotating shaft of the motor 14, and the gear wheel 141 meshes with the inner gear ring 24. The rotation of the rotating shaft of the motor 14 drives the gear wheel 141 to rotate, and the gear wheel 141 meshes with the inner gear ring 24 to drive the inner gear ring 24 to rotate in a horizontal plane at which the inner gear ring is located; and the inner gear ring 24 is fixedly provided at the upper end of the rotary tube 22, the inner gear ring 24 drives the rotary tube 22 to rotate, and further, the rotary tube 22 drives the plurality of scrapers 23 arranged inside the rotary tube 22 to rotate around the temperature control unit 21.

As shown in FIG. 1 and FIG. 2, a cooling unit 15 is fixedly provided at a position on an inner wall of the shell 1 corresponding to the fan-closed heating chamber 211. The reaction solution is separated into a water vapor and an evaporation residue at the outer wall of the fan-closed heating chamber 211, wherein the water vapor moves to the inner wall of the rotary tube 22 and is condensed; in order to condense the water vapor into liquid water fast and completely, a cooling unit 15 is fixedly provided at a position on the inner wall of the shell 1 corresponding to the fan-closed heating chamber 211; and a condensation medium may be water or air. If the fan-closed heating chamber 211 is 180° fan-shaped, the cooling unit 15 may also be 180° circular arc-shaped.

FIG. 4 is a schematic side view illustrating a structure of a scraper 23 of a device for producing a sucrose-6-ester according to an embodiment of the present disclosure. It can be seen from FIG. 4 that the scraper 23 is an L-shaped scraper. One end of the L-shaped scraper is an arrangement end 232 arranged at an upper end of the inner wall of the rotary tube; and with a direction in FIG. 4 as a benchmark, a vertical length of the arrangement end 232 can be determined according to factors such as the horizontal length and overall weight of the scraper and the height of the rotary tube, which should ensure that the scraper 23 can be firmly arranged on the inner wall of the rotary tube 22. In some embodiments, the vertical length of the arrangement end 232 may be ⅓ to ½ of the height of the rotary tube 22.

The other end of the L-shaped scraper 23 is an extension end 233 arranged in contact with an upper surface of the base 3, such that reaction solution droplets falling on the upper surface of the base 3 can also be scraped to the first feed port of the reaction channel 313.

In order to smoothly discharge the condensated water out from the device, a drainage port 25 is formed at a position on a lower end of the inner wall of the rotary tube 22 corresponding to each of L-shaped scrapers 23, a drainage plate 26 is provided corresponding to the drainage port 25, the drainage plate 26 and the rotary tube 22 are in non-contact arrangement, and the drainage plate 26, the corresponding drainage port 25, and a corresponding part of the rotary tube 22 form a condensated water channel. Because the scraper 23 has a drainage function, the water vapor is easily condensed at the scraper 23 and then flows downward. Thus, a condensated water channel provided under the scraper 23 makes it possible for condensated water flowing out of the device smoothly.

As shown in FIG. 1 and FIG. 2, in some embodiments of the present disclosure, the shell 1 is further provided with a vacuum tube 16, and the vacuum tube 16 is able to be connected to a vacuum pump. In order to well discharge the water vapor out from the device, the device can also be depressurized. Specifically, the vacuum tube 16 can be connected to a vacuum pump to achieve the above purpose.

FIG. 5 is a schematic sectional view illustrating a structure of a device for producing a sucrose-6-ester according to an embodiment of the present disclosure. It can be seen from FIG. 5 that the temperature control unit 21 is arranged against the upper surface of the base 3, and the temperature control unit 21 is divided into a heating chamber 211 and a cooling chamber 212 by a thermal insulation plate 213; the scrapers 23 are arranged on the inner wall of the rotary tube 22, and an outer edge of the scraper abuts against the outer wall of the temperature control unit 21; a drainage plate 26 and a corresponding drainage port 25 is provided under each scraper 23; and a cooling unit 15 is provided at a position on the inner wall of the shell 1 corresponding to the heating chamber 211, and a position on base 3 corresponding to a side of the cooling chamber 212 is provided with a reaction channel. Arrows in FIG. 5 indicate a movement direction of a material. Specifically, the reaction solution enters from the reaction solution inlet 13 of the shell 1, and the reaction solution is heated at the outer wall of the heating chamber 211 while being scraped into a liquid film, such that moisture in the reaction solution is evaporated out, moves along the scrapers 23 to the arrangement ends 232 of the scrapers 23 on the inner wall of the rotary tube 22, and is condensed into liquid water, and the liquid water flows downward along the scrapers 23 into the condensated water channel, then flows out of the rotary tube 22 through the drainage port 25, and then further flows out of the device through a condensated water outlet 11 of the shell 1. With the rotation and scraping of the rotary tube 22, the evaporation residue reaches an outer wall of the cooling chamber 212 and then gradually flows downward into the reaction channel 313 under the action of gravity.

FIG. 6 is a schematic diagram illustrating a 3D structure of a base 3 of a device for producing a sucrose-6-ester according to an embodiment of the present disclosure; and FIG. 7 is a schematic top view illustrating a structure of a base 3 of a device for producing a sucrose-6-ester according to an embodiment of the present disclosure.

As shown in FIG. 5, FIG. 6, and FIG. 7, the base 3 includes an upper base 31 and a lower base 32 that are arranged in close contact; the upper base is an uncapped cylinder including a side wall 311 and a bottom 312, a first feed port 316 is formed in an upper surface of the bottom 312, and the first feed port 316 may be arranged near a position corresponding to a junction between the heating chamber 211 and the cooling chamber 212; and similarly, the reaction solution inlet 13 of the shell 1 may also be provided in the same direction as the first feed port 316 and is close to a position corresponding to the junction between the heating chamber 211 and the cooling chamber 212, such that the reaction solution can undergo separation and cooling to the maximum degree.

A gradually-inclined circular reaction channel 313 is formed from an upper surface to a lower surface of the bottom 312 of the upper base 31; a first feed port 316 and a second feed port 315 are formed at an upwardly-inclined end of the reaction channel 313; the first feed port 316 is configured to receive the evaporation residue and the second feed port 315 is connected to a carboxylate feed pipe 314; and a discharge port 317 is formed at a downwardly-inclined end of the reaction channel, and connected to the reaction product discharge pipe 321 which penetrates through the lower base 32.

FIG. 8 is a schematic diagram illustrating a material flow direction of a base 3 of a device for producing a sucrose-6-ester according to an embodiment of the present disclosure. In some embodiments of the present disclosure, a rotation direction of the rotary tube 22 is opposite to an inclination direction of the reaction channel 313. It can be seen from FIG. 8 that, in this embodiment, the rotation direction of the rotary tube 22 is counterclockwise, and the inclination direction of the reaction channel 313 is clockwise. In this way, the evaporation residue can be thoroughly mixed with a carboxylic anhydride at an initial position of the reaction channel, and then a mixture of the evaporation residue and the carboxylic anhydride slowly flows downward in the reaction channel 313 under the action of gravity and can be subjected to an esterification reaction under preset conditions (such as a temperature of 0° C. to 20° C.) to obtain a sucrose-6-ester. The esterification reaction usually occurs at a reaction temperature that is not too high, such as about ambient temperature. Therefore, the reaction channel 313 may not be provided with a heating unit. In order to accelerate the reaction, a heating layer may also be arranged under the reaction channel 313 (not shown in the figures), which is not limited in the present disclosure and may be arranged as required.

FIG. 9 is a schematic flow chart of a method for producing a sucrose-6-ester according to an embodiment of the present disclosure. The method is implemented on any device described above, and at least includes the following steps S910 and S920:

S910: separation of reaction solution: the film scraping apparatus is started and a reaction solution is fed from the reaction solution inlet, such that the reaction solution is scraped into a liquid film by using the scrapers 23 to obtain an evaporation residue and a water vapor; the evaporation residue is allowed to flow into the reaction channel; and the water vapor is condensed into condensated water on the inner wall of the rotary tube and then allowed to flow out from the condensated water outlet, wherein the reaction solution includes sucrose, an aprotic polar solvent, and an organotin esterification accelerator; and S920: esterification reaction: the reaction solution entering the reaction channel is subjected to an esterification reaction with a carboxylate entering from a carboxylic anhydride inlet under preset conditions to obtain a sucrose-6-ester-containing solution.

In the method described above, in the present disclosure, there is no limitation on a rotational speed of the film scraping apparatus. In some embodiments of the present disclosure, the rotational speed of the film scraping apparatus may be 40 rpm to 100 rpm. If the rotational speed of the film scraping apparatus is less than 40 rpm, the reaction solution will flow downward too fast, such that the entire scraping separation process is too fast to sufficiently evaporate water; and if the rotational speed of the film scraping apparatus is greater than 100 rpm, the reaction solution will flow downward too slow, such that the overall reaction time is extended, which is not conducive to the rapid production of the sucrose-6-ester.

In the above methods, there is no limitation on the raw materials and preset conditions for the esterification reaction, which can refer to the prior art, or adopt those of the following recommended technical solutions.

In the present disclosure, there is no limitation on the type of the organostannide, and a monotin organic compound or a bitin organic compound can be used. In some embodiments, the organostannide is one or more selected from the group consisting of 1,3-dihydrocarbyloxy-1,1,3,3-tetra-(hydrocarbyl)distannoxane, tin di(hydrocarbyl)oxide, 1,3-diacyloxy-1,1,3,3-tetra-(hydrocarbyl)distannoxane, and 1-diacyloxy-1,1,3,3-tetra-(hydrocarbyl)distannoxane; in some other embodiments, the organostannide is 1,3-diacyloxy-1, 1,3,3-tetra-(hydrocarbyl)distannoxane; and in some other embodiments, the organostannide is 1,3-diacetoxy-1,1,3,3-tetrabutyldistannoxane. The hydrocarbyloxy is selected from the group consisting of alkoxy and phenoxy. In some embodiments, the alkoxy is selected from the group consisting of methoxy, ethoxy, n-propoxy, n-butoxy, n-pentoxy, and n-hexoxy; and in some other embodiments, the alkoxy is methoxy. In some embodiments, the hydrocarbyl is selected from the group consisting of alkyl, cycloalkyl, aryl, and aralkyl; in some other embodiments, the hydrocarbyl is alkyl; and in sonic other embodiments, the hydrocarbyl is n-butyl.

In the present disclosure, there is no limitation on the type of the aprotic polar solvent. In some embodiments, the aprotic polar solvent is one or more selected from the group consisting of acetonitrile, 1,4-dioxane, methyl ethyl ketone (MEK), methyl isobutyl ketone (MIK), nitromethane, nitroethane, cyclohexanone, dimethyl sulfoxide (DMSO), N-methylpyrrolidone (NMP), N,N-dimethylacetamide (DMA), hexamethylphosphoramide (HMPA), and N,N-dimethylformamide (DMF); and in some other embodiments, the aprotic polar solvent is acetonitrile.

In the present disclosure, there is no limitation on an amount of the aprotic polar solvent. In some embodiments, based on a mass of sucrose, a mass ratio of the aprotic polar solvent to sucrose is in a range of 2 to 20; in some other embodiments, the mass ratio of the aprotic polar solvent to sucrose is in a range of 3 to 10; and in some other embodiments, the mass ratio of the aprotic polar solvent to sucrose is in a range of 4 to 8.

In the present disclosure, there is no limitation on a heating temperature of the heating chamber. In some embodiments, the heating temperature may be in a range of 65° C. to 150° C.; and in some other embodiments, the heating temperature may be in a range of 85° C. to 120° C.

In the present disclosure, under the condition that the vacuum tube is connected to a vacuum pump, there is no limitation on a negative pressure in the device. In some embodiments, the negative pressure in the device may be maintained at 0.01 kPa to 50 kPa; and in some other embodiments, the negative pressure in the device may be maintained at 0.5 kPa to 20 kPa.

In the present disclosure, there is no limitation on the type of the carboxylic anhydride, and the carboxylic anhydride is one selected from the group consisting of acetic anhydride, butyric anhydride, benzoic anhydride, stearic anhydride, and lauric anhydride, and is preferably acetic anhydride. Sucrose-6-carboxylates resulting from the above types of organic acid anhydrides are respectively sucrose-6-acetate, sucrose-6-butyrate, sucrose-6-benzoate, sucrose-6-fatty acid ester, and sucrose-6-laurate. The sucrose-6-acetate and sucrose-6-benzoate can be used as raw materials for synthesizing other sucrose-6-carboxylates and as intermediates for synthesizing a sweetener sucralose; and the other types of sucrose-6-carboxylase can be used as food additives, chemical products, and synthetic intermediates for other reactions.

The present disclosure has no limitation on an amount of the carboxylic anhydride. In some embodiments, based on the mass of sucrose, a ratio of a mass of the carboxylic anhydride to the mass of sucrose is 0.6 to 3.0; and in some other embodiments, the ratio of the mass of the carboxylic anhydride to the mass of the sucrose is 0.8 to 1.

In the present disclosure, there is no limitation on the reaction conditions of the esterification reaction. In some embodiments, the esterification reaction may be conducted at a temperature of 0° C. to 50° C.; in some other embodiments, the esterification reaction may be conducted at a temperature of 1° C. to 20° C. In some embodiments, the esterification reaction may be conducted for 10 min to 24 h; and in some other embodiments, the esterification reaction may be conducted for 30 min to 4 h.

It should be noted that reaction conditions not detailed above may refer to the prior art.

Testing Methods and Reagent Sources Involved in the Present Disclosure

High-Performance Liquid Chromatography (HPLC) (for Testing the Contents of Substances in a Reaction Product Such as Sucrose and Sucrose-6-Ester)

High-performance liquid chromatograph of Shimadzu, Japan: RID-10A differential refractive index detection, LC-10ADVP high-pressure pump, and CTO-10ASVP incubator; chromatographic column: Agilent XDB C18 column (250 mm×4.6 mm, 5 μm); mobile phase: methanol-0.125% dipotassium phosphate (DKP) aqueous solution (4:6); column temperature: 30° C.; and flow rate: 1.0 mL/min. Methanol (chromatographically pure), DKP (analytically pure), ultrapure water (UPW), and sucralose (purity: 99.9%) are required, and a content is determined by an external standard method.

Moisture Test Method

A moisture content is determined by the Karl Fischer method, which can refer to the prior art and will not be repeated in various examples.

Reagent Sources

The chemical reagents involved in the present disclosure and raw materials for preparing a sucrose-6-ester may be commercially available, which are not limited in the present disclosure.

Example 1

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 300 kg of a reaction solution.

The device for preparing a sucrose-6-ester in the present disclosure was used to prepare a sucrose-6-ester, wherein the device had a diameter of 3 m; a temperature control unit had a radius of about 1.5 m; a radius ratio of a cooling chamber to a heating chamber was 10:9; 12 scrapers were arranged, and the scrapers each were made of manganese steel; and the device was connected to a vacuum pump.

A film scraping apparatus was started to make the film scraping apparatus rotate at a rotational speed of 40 rpm (about 10 rad/min). The reaction solution prepared above was continuously fed into the device at a rate of 4 m³/h. The reaction unit was maintained at a negative pressure of 0.5 kPa, and control switches of the cooling unit 15 of the shell and the heating chamber 211 and the cooling chamber 212 of the temperature control unit 21 were turned on; and the heating chamber 211 was set at a temperature of 80° C., and water was adopted as a cooling medium for the cooling unit 15 and the cooling chamber 212.

With a mass ratio of sucrose to acetic anhydride being 1:1.1, the acetic anhydride was introduced into the reaction channel at a temperature lower than 10° C. to allow an acylation reaction, and it took about 1 h from the beginning of mixing of the two to the final discharge of a reaction product from the reaction product outlet. A sucrose-6-ester-containing product flowing out from the reaction product outlet was collected.

A sample was taken from the evaporation residue before flowing into the reaction channel and tested for a moisture content, and the moisture content in this example was lower than 500 ppm.

Water was added with a volume ratio of the water to the reaction system being 0.25:1 to quench the reaction, and hexane was added with a volume ratio of hexane to the reaction system being 1:1 to extract the organotin esterification accelerator to obtain a sucrose-6-acetate solution. A content of each substance in the sucrose-6-acetate-containing solution was analyzed by HPLC. The normalization below and in the following examples means that, when a mixture is subjected to separation assay by HPLC, a sum of all substances is specified as 100%, and a percentage of each substance to all substances is determined according to a peak area. The product distribution was as follows:

a. sucrose-6-acetate: 90.01% (normalized);

b. diacetate: 8.45% (normalized); and c. sucrose: 0.30% (normalized).

Example 2

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 500 kg of a reaction solution.

The device for producing a sucrose-6-ester in the present disclosure was used to prepare a sucrose-6-ester, wherein the device had a diameter of 5 m; the temperature control unit had a radius of about 2.5 m; a radius ratio of the cooling chamber to the heating chamber was 15:13; 20 scrapers were arranged, and the scrapers each were made of manganese steel; and the device was connected to a vacuum pump.

A film scraping apparatus was started to make the film scraping apparatus rotate at a rotational speed of 50 rpm (about 8 rad/min). The reaction solution prepared above was continuously fed into the device at a rate of 4 m³/h. The reaction unit was maintained at a negative pressure of 0.5 kPa, and control switches of the cooling unit 15 of the shell and the heating chamber 211 and the cooling chamber 212 of the temperature control unit 21 were turned on; and the heating chamber 211 was set to a temperature of 80° C., and water was adopted as a cooling medium for the cooling unit 15 and the cooling chamber 212.

With a mass ratio of sucrose to acetic anhydride being 1:1.1, the acetic anhydride was introduced into the reaction channel at a temperature lower than 15° C. to allow an acylation reaction, and it took about 2 h from the beginning of mixing of the two to the final discharge of a reaction product from the reaction product outlet. A sucrose-6-ester-containing product flowing out from the reaction product outlet was collected.

A sample was taken from the evaporation residue before flowing into the reaction channel and tested for a moisture content, and the moisture content in this example was lower than 600 ppm.

Water was added with a volume ratio of water to the reaction system being 0.25:1 to quench the reaction, and hexane was added with a volume ratio of hexane to the reaction system being 1:1 to extract the organotin esterification accelerator to obtain a sucrose-6-acetate solution. A content of each substance in the sucrose-6-acetate-containing solution was analyzed by HPLC. The normalization below and in the following examples means that, when a mixture is subjected to separation assay by HPLC, a sum of all substances is specified as 100%, and a percentage of each substance to all substances is determined according to a peak area. The product distribution was as follows:

a. sucrose-6-acetate: 87.65% (normalized);

b. diacetate: 5.98% (normalized); and c. sucrose: 0.28% (normalized).

Example 3

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 500 kg of a reaction solution.

The device of a sucrose-6-ester in the present disclosure was used to prepare a sucrose-6-ester, wherein the device had a diameter of 5 m; the temperature control unit had a radius of about 2.5 m; a radius ratio of the cooling chamber to the heating chamber was 15:13; 20 scrapers were arranged, and the scrapers each were made of manganese steel; and the device was connected to a vacuum pump.

A film scraping apparatus was started to make the film scraping apparatus rotate at a rotational speed of 100 rpm (about 16 rad/min). The reaction solution prepared above was continuously fed into the device at a rate of 8 m³/h. The reaction unit was maintained at a negative pressure of 1 kPa, and control switches of the cooling unit 15 of the shell and the heating chamber 211 and the cooling chamber 212 of the temperature control unit 21 were turned on; and the heating chamber 211 was set to a temperature of 80° C., and water was adopted as a cooling medium for the cooling unit 15 and the cooling chamber 212.

With a mass ratio of sucrose to acetic anhydride being 1:1.1, the acetic anhydride was introduced into the reaction channel at a temperature lower than 20° C. to allow an acylation reaction, and it took about 2 h from the beginning of mixing of the two to the final discharge of a reaction product from the reaction product outlet. A sucrose-6-ester-containing product flowing out from the reaction product outlet was collected.

A sample was taken from the evaporation residue before flowing into the reaction channel and tested for a moisture content, and the moisture content in this example was lower than 650 ppm.

Water was added with a volume ratio of the water to the reaction system being 0.25:1 to quench the reaction, and hexane was added with a volume ratio of hexane to the reaction system being 1:1 to extract the organotin esterification accelerator to obtain a sucrose-6-acetate solution. A content of each substance in the sucrose-6-acetate-containing solution was analyzed by HPLC. The normalization below and in the following examples means that, when a mixture is subjected to separation assay by HPLC, a sum of all substances is specified as 100%, and a percentage of each substance to all substances is determined according to a peak area. The product distribution was as follows:

a. sucrose-6-acetate: 88.96% (normalized);

b. diacetate: 7.86% (normalized); and c. sucrose: 0.24% (normalized).

Comparative Example 1

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 300 kg of a reaction solution, and the reaction solution was heated to a temperature of 90° C. for dissolution to obtain a reaction mixed solution.

A packed tower was used for dehydration, wherein the packed tower had a diameter of 40 mm and was packed with a 3×8 glass spring packing at a packing height of 1 m, which was equivalent to 10-stage tower plates.

The reaction mixed solution prepared above was fed from an inlet at a top of the packed tower which was maintained at a negative pressure of 0.5 kPa; and a cyclohexane vapor (100° C., 4 atm) was fed from a flask gas inlet at a bottom of the packed tower. The reaction mixed solution and the cyclohexane vapor were in countercurrent contact to allow a reaction. A distillate (a vapor including cyclohexane, water, and DMF) discharged from the top of the packed tower was condensed, collected, dried to remove water, and then recycled.

A liquid sample was collected in a flask at the bottom of the packed tower, which was transparent and light-amber. A retention time of the reaction solution in a gas-liquid exchange reactor was about 1 min.

A sucrose content of a resulting solution was calculated to be 10%. The resulting solution was pressed into another reactor, then acetic anhydride was added dropwise at a temperature lower than 10° C. with a mass ratio of sucrose to acetic anhydride being 1:1.1 to allow an acylation reaction at a temperature lower than 10° C. for 2 h, and then water was added according to a ratio of 0.25:1 for quenching the reaction; and cyclohexane was added according to a ratio of 1:1 for extracting the organostannide, and a resulting sucrose-6-acetate solution was analyzed by HPLC. Analysis results of the products were as follows:

a. sucrose-6-acetate: 72.05% (normalized);

b. diacetate: 4.36% (normalized); and c. sucrose: 22.76% (normalized).

It can be seen from Examples 1 to 3 and Comparative Example 1 that, compared with the packing and falling liquid production device in Comparative Example 1, the production device provided in the present disclosure can lead to a high sucrose-6-carboxylate yield, a low side reaction occurrence probability, and a complete sucrose reaction. It can be seen that the sucrose-6-acetate yield can reach 90.01% (normalized) in some examples of the present disclosure, but is only 72.05% (normalized) in Comparative Example 1. That is, the sucrose-6-carboxylate yield in the present disclosure is significantly higher than that in the prior art. Similarly, from the diacetate and sucrose contents in the reaction products, it can be seen that the side reaction occurrence probability of the present disclosure is significantly reduced, and the conversion of sucrose in the present disclosure is more thorough.

In summary, the present disclosure has the following beneficial effects:

A production device provided with a film scraping apparatus is designed. The rotation of the film scraping apparatus scrapes a reaction solution into a liquid film, such that moisture can be quickly evaporated and condensed to achieve the purpose of removing moisture from the reaction solution, which overcomes the defect in the prior art that, during a process of removing moisture from a first reaction mixture, a large amount of a gas or solvent vapor capable of removing water is required. With the design of the present disclosure, an evaporation residue separated from the reaction solution can be pressed into a reactor without additional power to react with a carboxylic anhydride in the reactor, which reduces the electrical energy consumption and the volume and floor space of the production device and overcomes the defect in the prior art that a second reaction mixture needs to be injected into another space and mixed with a carboxylic anhydride. In the present disclosure, the reaction raw materials can be continuously fed into the production device, and the reaction solution separation and esterification reaction steps can be conducted uninterruptedly, such that the sucrose-6-ester can be continuously produced, which greatly shortens the production cycle and improves the production efficiency of the sucrose-6-ester. Moreover, due to the thorough moisture removal, the sucrose-6-ester yield is significantly improved.

The above are merely specific implementations of the present disclosure, and under the above teaching of the present disclosure, those skilled in the art may make other improvements or variations on the basis of the above examples. Those skilled in the art should appreciate that the above specific description is merely intended to well explain the purpose of the present disclosure, and a protection scope of the present disclosure shall be subject to the protection scope of the claims.

In addition, those skilled in the art can understand that, although some embodiments herein include some features included in other embodiments but no other features, a combination of features of different embodiments falls within the scope of the present disclosure and forms a different embodiment. For example, in the claims, any one of the claimed embodiments can be used in any combination.

What is claimed is:

1. A device for producing a sucrose-6-ester, comprising:
a shell;
a film scraping apparatus; and
a base, wherein
the film scraping apparatus is on the base, wherein the shell covers the film scraping apparatus and the base;
the shell comprises a reaction solution inlet and a condensed water outlet; the base comprises a carboxylate feed pipe, a reaction product discharge pipe, and a reaction channel connected to the carboxylate feed pipe;
the film scraping apparatus comprises a temperature control unit, a rotary tube, and a plurality of scrapers arranged on an inner wall of the rotary tube, wherein an outer edge of each of the plurality of scrapers abuts against an outer wall of the temperature control unit;
the rotary tube is able to rotate around the temperature control unit, such that a reaction solution entering from the reaction solution inlet and flowing downward along the outer wall of the temperature control unit can be scraped into a liquid film on the outer wall of the temperature control unit, wherein the plurality of scrapers are configured to obtain an evaporation residue and a water vapor; and
the temperature control unit is a cylindroid that is arranged coaxially with the rotary tube and composed of a fan-closed heating chamber and a fan-closed cooling chamber, wherein the fan-closed heating chamber and the fan-closed cooling chamber are separated by a thermal insulation plate.

2. The device of claim 1, wherein a diameter of the fan-closed cooling chamber is greater than a diameter of the fan-closed heating chamber;
wherein the plurality of scrapers are elastic metal sheets, and outer edge ends of the plurality of scrapers are arc-shaped.

3. The device of claim 1, wherein the rotary tube comprises a fixed, inner gear ring at an upper end of the rotary tube;

the shell comprises a motor penetrating through the shell, and the motor comprises a gear wheel at an end of a rotating shaft of the motor; and
the gear wheel is configured to mesh with the inner gear ring.

4. The device of claim 1, wherein a cooling unit is fixed at a position on an inner wall of the shell corresponding to the fan-closed heating chamber.

5. The device of claim 1, wherein the plurality of scrapers are L-shaped scrapers; one end of each of the L-shaped scrapers is an arrangement end arranged at an upper end of the inner wall of the rotary tube, and the other end of each of the L-shaped scrapers is an extension end arranged in contact with an upper surface of the base; and
a drainage port is at a position on a lower end of the inner wall of the rotary tube corresponding to each of the L-shaped scrapers, a drainage plate corresponding to the drainage port, wherein the drainage plate, the corresponding drainage port, and a corresponding part of the rotary tube form a condensed water channel.

6. The device of claim 1, wherein the base comprises an upper base and a lower base that are arranged in contact;
a gradually-inclined circular reaction channel extends from an upper surface to a lower surface of a bottom of the upper base;
a first feed port and a second feed port are at an upwardly-inclined end of the reaction channel, and the first feed port is configured to receive the evaporation residue and the second feed port is connected to the carboxylate feed pipe; and
a discharge port at a downwardly-inclined end of the reaction channel, and the discharge port is connected to the reaction product discharge pipe penetrating through the lower base.

7. The device of claim 6, wherein a rotation direction of the rotary tube is opposite to an inclination direction of the reaction channel.

8. The device of claim 1, wherein the shell further comprises a vacuum tube, and the vacuum tube is configured to connect to a vacuum pump.

\* \* \* \* \*